United States Patent
Czygan

(10) Patent No.: US 7,450,990 B2
(45) Date of Patent: Nov. 11, 2008

(54) STIMULATION DEVICE WITH STIMULATION OUTCOME MONITORING

(75) Inventor: Gerald Czygan, Buckenhof (DE)

(73) Assignee: Biotronik GmbH & Co. KG (DE)

(*) Notice: Subject to any disclaimer, the term of this patent is extended or adjusted under 35 U.S.C. 154(b) by 459 days.

(21) Appl. No.: 10/695,661

(22) Filed: Oct. 28, 2003

(65) Prior Publication Data
US 2004/0147983 A1    Jul. 29, 2004

(30) Foreign Application Priority Data
Oct. 30, 2002  (DE) ................. 102 50 996

(51) Int. Cl.
A61N 1/00 (2006.01)
A61N 1/36 (2006.01)
A61N 1/37 (2006.01)

(52) U.S. Cl. .............................. 607/28
(58) Field of Classification Search .......... 607/6–9, 607/11, 13, 27–28; 600/481, 547
See application file for complete search history.

(56) References Cited

U.S. PATENT DOCUMENTS

| | | | |
|---|---|---|---|
| 4,114,627 A * | 9/1978 | Lewyn et al. ............. | 607/13 |
| 4,245,643 A * | 1/1981 | Benzing et al. ............ | 607/28 |
| 4,686,988 A * | 8/1987 | Sholder .................. | 607/28 |
| 5,033,473 A * | 7/1991 | Wang et al. .............. | 600/509 |
| 5,233,985 A * | 8/1993 | Hudrlik ................. | 607/27 |
| 5,350,410 A | 9/1994 | Kleks et al. | |
| 5,405,365 A * | 4/1995 | Hoegnelid et al. ......... | 607/28 |
| 5,411,533 A | 5/1995 | Dubreuil et al. | |
| 5,431,639 A | 7/1995 | Shaw | |
| 5,431,693 A * | 7/1995 | Schroeppel .............. | 607/28 |
| 5,454,377 A * | 10/1995 | Dzwonczyk et al. ....... | 600/547 |
| 5,674,254 A | 10/1997 | van Krieken | |
| 5,713,931 A * | 2/1998 | Paul et al. .............. | 607/27 |
| 5,713,933 A | 2/1998 | Condie et al. | |
| 5,735,883 A | 4/1998 | Paul et al. | |
| 5,766,230 A * | 6/1998 | Routh et al. ............. | 607/27 |
| 5,800,469 A * | 9/1998 | Nappholz ............... | 607/18 |
| 5,843,137 A * | 12/1998 | Condie et al. ............ | 607/28 |
| 6,141,585 A * | 10/2000 | Prutchi et al. ............ | 607/8 |
| H1929 H * | 12/2000 | Citak .................... | 607/28 |
| 6,238,419 B1 * | 5/2001 | Lindgren ............... | 607/9 |
| 6,304,781 B1 * | 10/2001 | Busch et al. ............. | 607/28 |

(Continued)

FOREIGN PATENT DOCUMENTS

DE      41 26 363    2/1993

(Continued)

Primary Examiner—Kennedy J. Schaetzle
Assistant Examiner—Jessica Reidel
(74) Attorney, Agent, or Firm—Hahn Loeser & Parks LLP

(57) ABSTRACT

A device for electrostimulation of body tissue through a stimulation electrode, in which a stimulation outcome is detected, at least after delivery of a stimulation pulse, on the basis of detecting a drop in a voltage over time or a rise in a short-circuit current over time at a capacitance including at least one Hemholtz capacitance produced on the surface of the stimulation electrode in conjunction with surrounding body fluid or the body tissue, and wherein the drop in voltage or the rise in short-circuit current is representative of a characteristic drop in a myocardium impedance of the body tissue.

40 Claims, 4 Drawing Sheets

U.S. PATENT DOCUMENTS

| | | | | |
|---|---|---|---|---|
| 6,522,924 | B1 * | 2/2003 | Meier | 607/28 |
| 2001/0049543 | A1 * | 12/2001 | Kroll | 607/28 |
| 2002/0123773 | A1 * | 9/2002 | Molin | 607/27 |
| 2002/0147477 | A1 * | 10/2002 | Pons et al. | 607/27 |
| 2003/0009200 | A1 * | 1/2003 | Noren et al. | 607/28 |

FOREIGN PATENT DOCUMENTS

| | | |
|---|---|---|
| DE | 197 49 719 | 5/1999 |
| EP | 0 399 063 | 5/1989 |
| EP | 1 062 979 A2 * | 12/2000 |

* cited by examiner

STIMULATION DEVICE WITH STIMULATION OUTCOME MONITORING

The invention concerns a device for electrostimulation of body tissue, in particular a cardiac pacemaker. The electrostimulation device has an energy source for providing electrical stimulation energy, an electrode connection for connecting a stimulation electrode for the delivery of electrical stimulation pulses and a switch with which the energy source is connected to the electrode connection for the delivery of a stimulation pulse. The electrostimulation device further has a means for stimulation outcome monitoring. In addition the electrostimulation device includes a short-circuit switch with which the electrode connection after delivery of the stimulation pulse is to be at least indirectly connected to a ground potential in such a way that in the case of a connected and implanted electrode line a capacitance can be discharged by way of the body tissue and a ground electrode in such a way that a short-circuit current flows through the body tissue, wherein the capacitance includes at least one Helmholtz capacitance which occurs on the surface of the stimulation electrode in conjunction with surrounding body fluid or body tissue. The electrostimulation device also includes a control unit which is connected at least to the first switch and the short-circuit switch for switching over those switches and is adapted to separate the electrode line connection from the energy source after delivery of the stimulation pulse and at least indirectly connect it to the ground potential.

BACKGROUND OF THE ART

Electrostimulation devices of the above-specified kind are already known in particular in the form of implantable cardiac pacemakers. Such pacemakers in the implanted and operable condition are usually connected by way of an electrode line of the above-specified kind to an electrode disposed in the heart, and adapted to deliver electrical stimulation pulses to the heart by way of the electrode. Those stimulation pulses serve to excite the heart tissue or myocardium and depending on the respective kind of pacemaker are delivered in particular when the heart does not contract naturally at the right time. A contraction is then caused by an electrical pulse which is delivered to the myocardium. If that electrical pulse is of sufficient magnitude, it has the effect that the heart muscle tissue is locally depolarised and correspondingly contracts. Depolarisation and contraction of the heart muscle tissue is intended to extend over all of the stimulated heart muscle and thus lead to the desired contraction of the corresponding chamber of the heart.

The corresponding electrical stimulation pulse must be of a stimulation intensity which is above a respective stimulus threshold of the heart muscle tissue. In that respect the stimulus threshold is a measurement in respect of the minimum stimulation intensity which is sufficient to cause depolarisation of the myocardium and thus a contraction of a respective chamber of the heart. The stimulus threshold depends on various factors and in addition is also variable under some circumstances with the passage of time. With the requirement of delivering a stimulation pulse of adequate stimulation intensity, there is also the need to minimise the energy to be applied for a stimulation pulse. That energy is usually taken from a battery of the cardiac pacemaker which becomes exhausted as time passes. When that battery is exhausted an implanted cardiac pacemaker has to be replaced by a new one in an operative procedure. It is therefore desirable for the cardiac pacemaker to have the longest possible operating time and thus for the battery to have the longest possible service life. In addition the energy for a stimulation pulse should also therefore be as low as possible but sufficient to stimulate only the myocardium but not surrounding muscle tissue.

There is therefore on the one hand the requirement that the intensity of stimulation of a stimulation pulse must suffice to trigger a contraction of the heart muscle tissue. A higher level of stimulation intensity, with other influencing parameters unaltered, entails a higher degree of energy consumption. The stimulation intensity depends on the one hand on the duration of a stimulation pulse and on the other hand on the strength of a stimulation pulse. The strength of a stimulation pulse in turn depends on the electrical voltage with which a stimulation pulse is delivered to the heart muscle tissue. Therefore, a higher level of stimulation intensity usually also results in a higher degree of energy consumption. In order to achieve reliable stimulation of the heart muscle tissue, stimulation pulses are regularly delivered, which from the point of view of energy cost rather more energy than would be necessary as a minimum.

On the other hand, there is a need for the energy consumption per stimulation pulse to be kept as low as possible as that energy is taken from a battery of the cardiac pacemaker, which in that way becomes exhausted.

There is therefore the need to satisfy the requirements for a level of stimulation intensity which is as low as possible and at the same time regular successful stimulation, by optimisation of the stimulation intensity. For that purpose, it is known from the state of the art, for example from U.S. Pat. Nos. 5,350,410; 5,411,533; 5,431,639; and 5,674,254, after delivery of a stimulation pulse, to detect the stimulation outcome (capture) (this being referred to as capture recognition), in order to trigger a back-up stimulation pulse if possible in the event of a defective stimulation outcome or capture.

It is also known for a stimulation outcome to be detected by detecting the impedance of the heart muscle tissue. In this connection attention is to be directed to U.S. Pat. Nos. 5,713,933; 5,735,883; and 5,766,230, and European patent application No. 0 399 063.

In spite of the many known proposals for stimulation outcome monitoring and for automatically adapting the stimulation pulse intensity, there is still the need for a device which is reliable in that respect.

The object of the invention is to afford a suitable device at least as an alternative to the known state of the art.

SUMMARY OF THE INVENTION

In accordance with the invention that object is attained by an electrical stimulation device of the kind set forth in the opening part of this specification, in which the means for stimulation outcome monitoring, at least after delivery of a stimulation pulse, is connected to the electrode connection and is adapted to detect the configuration in respect of time of a voltage at the capacitance after delivery of the stimulation pulse or of the short-circuit current flowing by virtue of said voltage or a further parameter linked to one of the parameters. The invention therefore aims to short-circuit a capacitance which is charged during delivery of a stimulation pulse—whether it is the Helmholtz capacitance which is formed on the surface of the stimulation electrode or another capacitance—after delivery of the stimulation pulse by way of the heart muscle tissue and to detect the corresponding short-circuit voltage or the short-circuit current or a parameter derived therefrom for determining the myocardium impedance.

An advantage of that stimulation outcome monitoring procedure is that the result of the outcome monitoring operation can be attained in a very short time so that a back-up pulse is to be triggered in a very short time in the event of a lack of stimulation success.

A preferred electrostimulation device is one in which the means for stimulation outcome monitoring is adapted to detect a corresponding drop in the configuration in respect of time of the detected voltage or a rise in the short-circuit current or a corresponding change in the linked parameter. That preferred means for stimulation outcome monitoring is thus so designed that it detects a stimulation outcome on the basis of a temporary and short-term characteristic drop in the myocardium impedance, which leads to a corresponding drop in the short-circuit voltage or a rise in the short-circuit current. Such a short-term drop in the myocardium impedance is a sign of successful, that is to say super-threshold stimulation of the heart muscle tissue. The terms 'super-threshold' on the one hand and 'sub-threshold' on the other hand characterise stimulation pulses which on the one hand are of a sufficient intensity to cause a contraction of the heart muscle tissue or on the other hand are not of sufficient intensity for successfully stimulating the heart muscle tissue.

In a preferred embodiment of the electrostimulation device the capacitance includes a coupling capacitor which is connected into circuit when the short-circuit switch is closed between the electrode connection and the ground electrode. Such a coupling capacitor is usually employed in cardiac pacemakers to produce, after delivery of a stimulation pulse, a flow of current in the opposite direction through the myocardium so that pure ac stimulation of the myocardium takes place and direct currents are avoided. For that purpose during the delivery of a stimulation pulse the coupling capacitor is connected in series with a reservoir capacitor and the electrode for delivery of the stimulation pulse. The reservoir capacitor contains the energy for the stimulation pulse. It is delivered to the myocardium by way of the coupling capacitor and electrodes. In that situation the coupling capacitor is charged by way of the stimulation pulse. After delivery of the stimulation pulse the coupling capacitor is short-circuited by way of the myocardium so that the above-mentioned flow of current through the myocardium takes place, which is in the opposite direction to the flow of current during delivery of the stimulation pulse. That flow of current through the myocardium after delivery of the stimulation pulse is detected by the means for stimulation outcome monitoring and evaluated in regard to an impedance breakdown in the myocardium.

For the last-mentioned purpose the means for stimulation outcome monitoring is preferably so arranged and designed that it detects the voltage at the coupling capacitor.

Irrespective of the presence of a coupling capacitor, that is to say even when the capacitance in question is the Helmholtz capacitance which is formed on the surface of the stimulation electrode, the means for stimulation outcome monitoring is preferably connected in such a way that it detects the current strength of the short-circuit current or the voltage at the electrode connection, which is applied at the capacitance.

If a coupling capacitor is provided, the means for stimulation outcome monitoring is suitably connected in such a way that it detects the current strength of the short-circuit current or the voltage applied at the capacitance, between the coupling capacitor and the electrode connection.

In order to detect the above-discussed short-term reduction in myocardium impedance as an indication of successful stimulation, the means for stimulation outcome monitoring preferably includes a differentiating member for differentiating the detected voltage or the detected current strength. In a particularly preferred alternative embodiment that differentiating member is connected to a threshold value detector in such a way that the means for stimulation outcome monitoring detects a drop in the detected voltage, which is above a predetermined limit value, more particularly preferably by detecting when the derivative of the detected voltage falls below a threshold value.

A particularly preferred embodiment of the means for stimulation outcome monitoring is one which by means of the differentiating member generates a derivative of the detected voltage and for example standardises it by division to the detected voltage. The signal generated in that way is then analysed in relation to a threshold criterion.

Irrespective of the details of the means for stimulation outcome monitoring, that means is preferably connected to a timer which is to be started with the delivery of a stimulation pulse and which ascertains the period of time up to the detection of stimulation outcome. That embodiment is based on the realisation that the extent to which the stimulation pulse is super-threshold is to be derived from the period of time between the delivery of a stimulation pulse and the occurrence of the stimulation outcome. With a minimally sufficient stimulation intensity, the time interval between the delivery of the stimulation pulse and the occurrence of the stimulation outcome is greater than when the situation involves a stimulation intensity which is considerably greater than the minimally required level.

In accordance with the above-indicated realisation, a preferred embodiment of the electrostimulation device is one in which the timer outputs a time signal corresponding to the time duration between the delivery of a stimulation pulse and the occurrence of the stimulation outcome, and is connected to a stimulation strength control unit which responds to the time signal and causes adjustment of the strength of the stimulation pulse (the stimulation pulse intensity) in dependence on the time signal.

In a particularly preferred alternative configuration the stimulation strength control unit is adapted to control the intensity of a stimulation pulse in dependence on the time measured by the timer upon the delivery of a preceding stimulation pulse, in such a way that said time is maximised within a predetermined time window.

In conjunction with all the above-described embodiments it is advantageously provided that the ground electrode is formed by a housing of the electrostimulation device or a surface portion of said housing.

The energy source of the electrical stimulation device preferably includes a reservoir capacitor and particularly preferably a charge pump for charging the reservoir capacitor. Control of charging of the reservoir capacitor and delivery of the stimulation pulse is preferably implemented by switches which are so designed and are to be connected to the reservoir capacitor that the reservoir capacitor is connected to the electrode connections, for charging with the charge pump and for delivering a stimulation pulse.

Further details of preferred configurations are to be found in the description hereinafter of an embodiment by way of example.

BRIEF DESCRIPTION OF THE DRAWINGS

The embodiments by way of example are described in greater detail hereinafter with reference to the drawings in which.

DETAILED DESCRIPTION OF A PREFERRED EMBODIMENT

Figure 1:
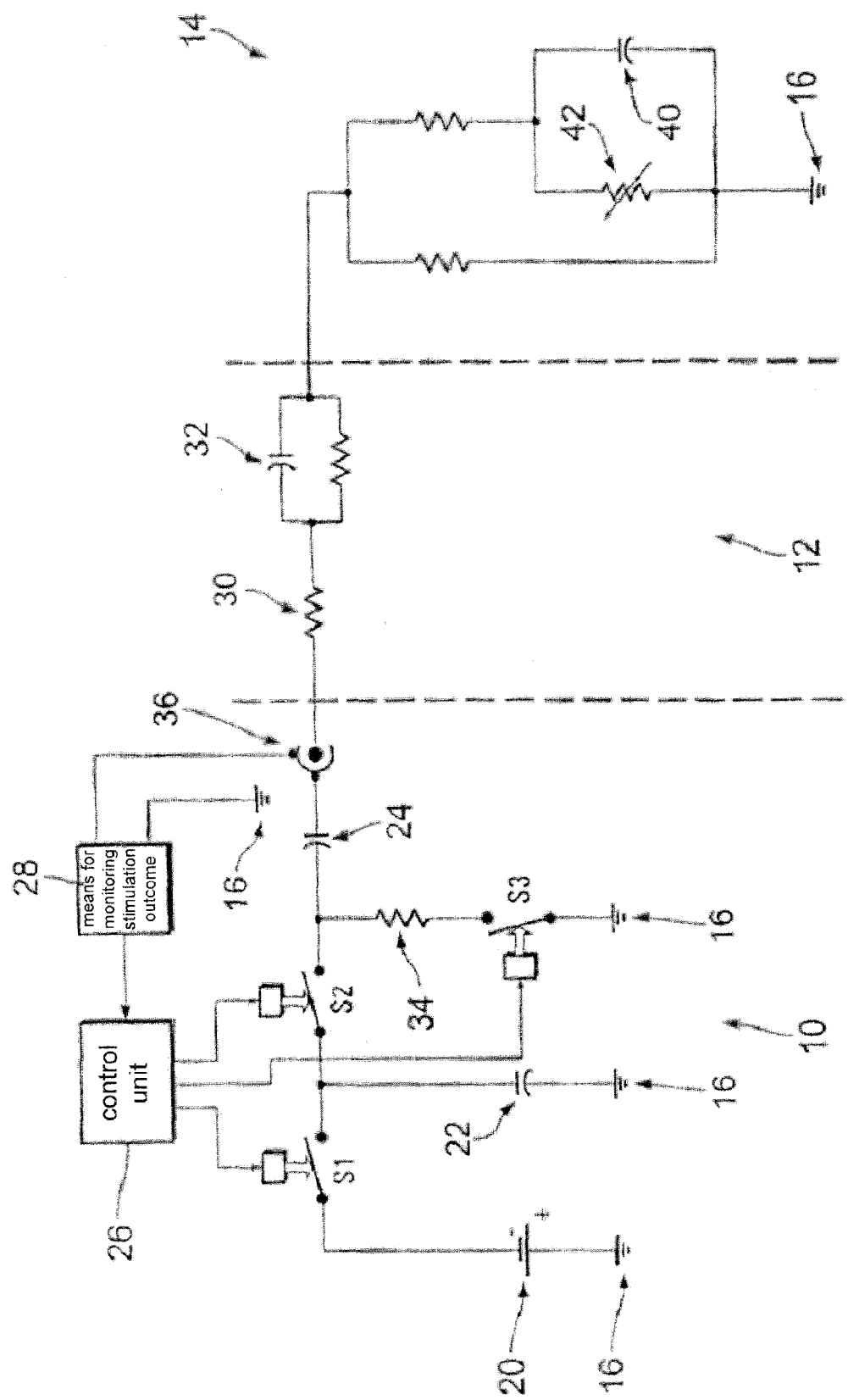
FIG. 1 shows a diagrammatic view of the essential components of an electrostimulation unit and an electrical equivalent circuit diagram for an electrode line connected to the stimulation unit and the myocardium communicating with the electrostimulation unit and the electrode line.

Shown in FIG. 1 to the left of the left-hand broken line is a diagrammatic view of an electrostimulation unit such as for example an implantable cardiac pacemaker, cardioverter or defibrillator.

Illustrated between the two broken lines is an electrical equivalent circuit diagram for an electrode line 12 connected to the electrostimulation unit 10.

Shown to the right of the right-hand broken line in FIG. 1 is an equivalent circuit diagram for the heart muscle tissue 14 (myocardium) which is electrically connected to an electrode of the electrode line 12 and a neutral or ground electrode 16 of the electrostimulation unit 10.

The essential components of the electrostimulation unit 10 are an energy source 20 which usually includes a charge pump (not shown), a reservoir capacitor 22, a coupling capacitor 24, a control unit 26 and a means 28 for stimulation outcome monitoring.

The energy source 20 is generally in the form of a charge pump with which it is possible to produce an adjustable voltage which can also be over the output voltage of a supply battery. The symbol in the drawing thus represents a supply battery with downstream-connected charge pump.

The reservoir capacitor 22 is connected by way of a switch S1 to the energy source 20 in such a way that it is connected in parallel with the energy source 20 and is charged thereby.

In addition the reservoir capacitor 22 is to be connected by way of a switch S2 by way of the coupling capacitor 24 to the electrode line 12 for the delivery of a stimulation pulse to the myocardium 14.

Besides an ohmic electrode resistance 30 the electrode line has a Helmholtz capacitance 32 which is formed in known manner on the surface of a stimulation electrode. Upon the delivery of an electrostimulation pulse with the switch S2 closed and the switches S1 and S3 open the coupling capacitor 24 is connected in series into the Helmholtz capacitance 32.

Prior to delivery of an electrostimulation pulse to the myocardium 14 the reservoir capacitor 22 is firstly charged up by the switch S1 being closed. The switch S1 is then opened and the switch S2 closed for the delivery of the electrostimulation pulse. The reservoir capacitor 22 is then discharged by way of the coupling capacitor 24 and the electrode line 12 with its Helmholtz capacitance 32 and by way of the myocardium 14. For that purpose the reservoir capacitor 22 is connected on the one hand to the electrode line 12 and on the other hand to a neutral electrode which is in the form of a ground electrode 16 and is electrically connected to the myocardium 14. The neutral electrode can be formed for example by a cardiac pacemaker housing so that the electrostimulation pulse is unipolarly delivered. The neutral electrode however can also be formed by a separate electrode on the electrode line 12 so that the electrostimulation pulse is delivered in bipolar mode.

After delivery of the electrostimulation pulse the switch S2 is opened again and the switch S3 closed. In that way the coupling capacitor 24 is short-circuited by way of an ohmic resistor 34 and the neutral electrode 16 on the one hand and by way of the electrode line 12 and the myocardium 14 on the other hand. That so-called autoshort of the stimulation electrode by closing the switch S3 causes discharging of the Helmholtz capacitance 32 formed by the interface between the electrode 16 and the body tissue and permits sensing after delivery of the stimulation pulse. In that respect the term sensing is used to denote the detection of electrical potentials in the myocardium, as are also recorded for example for an intracardial electrocardiogram.

Therefore, for the delivery of an electrostimulation pulse the switches S1, S2 and S3 are successively closed and opened again in that sequence, before the next switch is closed. Closing and opening of the switches S1, S2 and S3 is produced by the control unit 26.

The means 28 for stimulation outcome monitoring is electrically connected to an electrode line connection 36 disposed between the coupling capacitor 24 and the electrode line 12. The means 28 for stimulation outcome monitoring is adapted to detect the voltage at the electrode line connection 36 in relation to the ground potential and for that purpose it is connected to the neutral electrode 16.

Detection of the voltage at the electrode line connection 36 for the purposes of stimulation outcome monitoring can be effected both during the delivery of an electrostimulation pulse with the switch S2 closed and the switch S3 open and also after delivery of the electrostimulation pulse with the switch S2 open and the switch S3 closed. The case which is of interest here is the last-mentioned one.

In specific terms for example at the time t=1 s a stimulus of 2.4 V is delivered, that is to say S2 is closed. The stimulus is 0.5 ms long, then S2 is opened again and at the same time S3 is closed for autoshort purposes. The autoshort time is 10 ms long, thereafter S3 is open again. During the discharge depolarisation occurs after 5 ms, the membrane resistance abruptly changes for 1 ms. In the measured voltage pattern, the membrane resistance change is expressed in terms of an altered time constant in respect of discharge. After depolarisation however the electrode is discharged with the original time constant to another level. The curve therefore produces a slight jump corresponding to the abrupt membrane resistance.

The means 28 for stimulation outcome monitoring is connected to the control unit 26 and delivers a respectively different signal to the control unit 26, depending on whether the means 28 for stimulation outcome monitoring has or has not detected successful electrostimulation. If, after the delivery of a stimulation pulse on the part of the means 28 for stimulation outcome monitoring, there is no signal at the corresponding input of the control unit 26, the control unit 26 implements automatic adaptation of the stimulation pulse intensity by increasing the pulse voltage or by prolonging the pulse duration.

In that respect the control device 26 can be so designed that, in the absence of a signal characterising a stimulation success, on the part of the means 28 for stimulation outcome monitoring, a second stimulation pulse of greater energy is immediately delivered as a back-up pulse.

Detection of a stimulation outcome by the means 28 for stimulation outcome monitoring is effected by evaluation of the voltage applied at the electrode line connection 36. Upon successful electrostimulation that voltage briefly breaks down, as in the event of successful stimulation, indicating that the impedance of the myocardium, shown in FIG. 1 by a parallel connection of a capacitance 40 and a variable ohmic resistance 42, temporarily changes in such a way that the ohmic resistance 42 of the myocardium decreases for a moment because the ion channels, in particular the sodium channels of the muscle cells, open. That dip in impedance is detected by the means 28 for stimulation outcome monitoring and evaluated in such a way that the means 28 for stimulation outcome monitoring delivers a signal characterising stimulation success, to the control unit 26.

Figure 4:
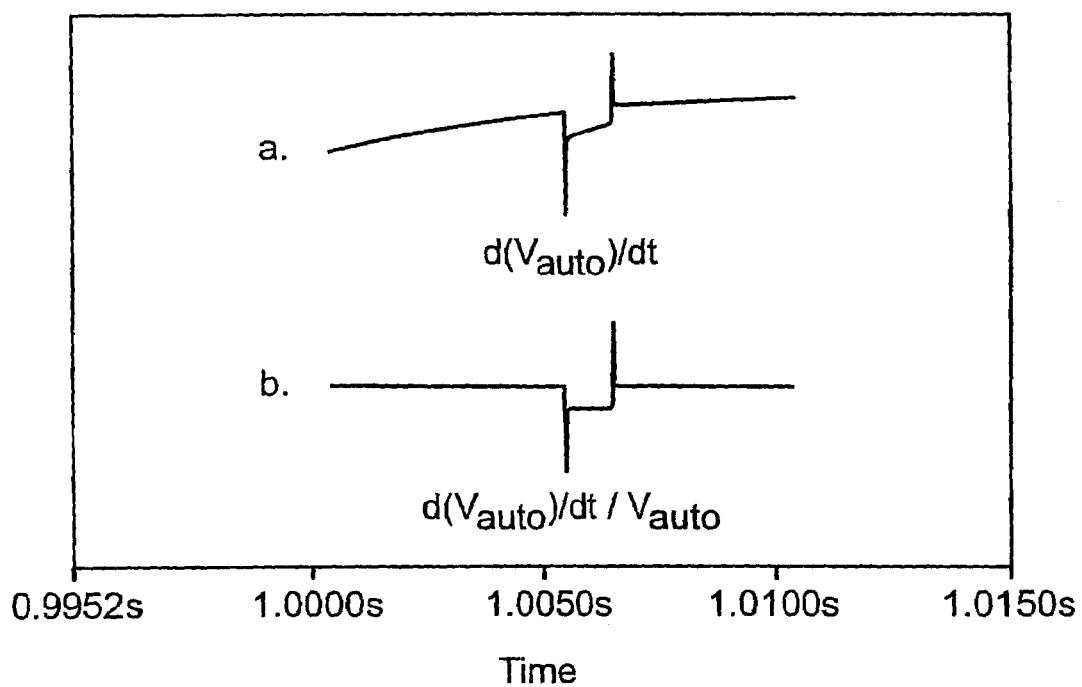

As the effects of the change in membrane resistance are slight, depolarisation can possibly only be detected with difficulty from the configuration of the discharge voltage itself. In order better to recognise the jump in the time constant, the curve can be differentiated (FIG. 4, curve a) or the differentiated curve can additionally also be divided by the initial curve (FIG. 4, curve b).

Figure 2:
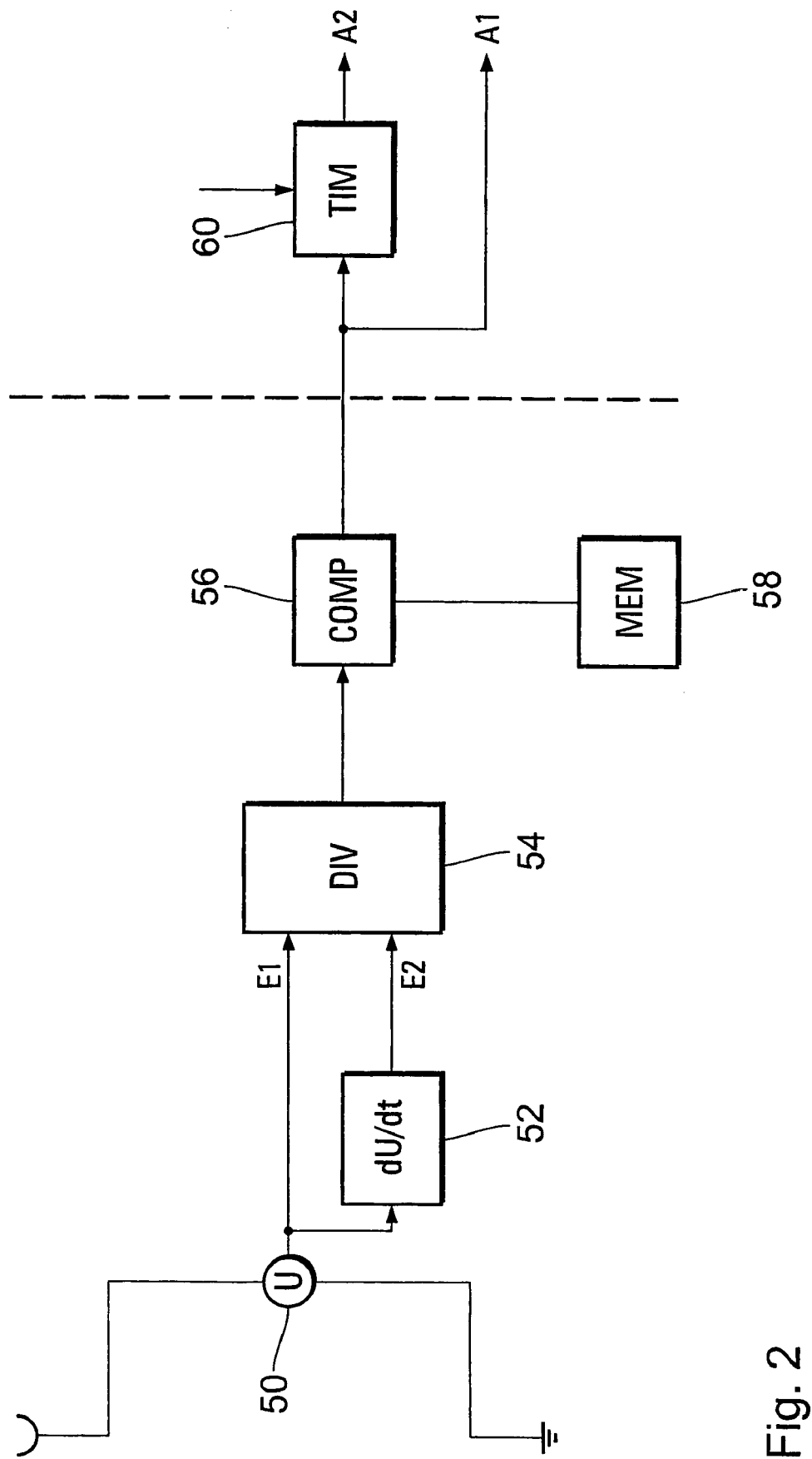
FIG. 2 shows a diagrammatic view of a means for stimulation outcome monitoring of the electrostimulation unit of FIG. 1.

In a preferred embodiment the means 28 for stimulation outcome monitoring detects both the voltage between the neutral electrode 16 and the electrode line connection 36 by way of a voltage measuring unit 50 (see FIG. 2) and also the derivative of that voltage with respect to time. For that purpose a differentiating member 52 is connected downstream of the voltage measuring unit 50. The derivative of the detected voltage is standardised to the detected voltage by way of a dividing member 54. For that purpose the dividing member 54 receives both the output signal from the differentiating member 52 at an input E2 and also the voltage detected by the voltage measuring unit 50 at an input E1 of the dividing member 54. In the dividing member 54 the value at the input E2 (the derivative of voltage with respect to time) is divided by the value at the input E1 (the detected voltage). The signal at the output of the dividing member 54 is passed to a threshold value detector which is formed by a comparator 56 and a threshold value memory 58. If the output value of the dividing member 54 exceeds the comparative value (threshold) stored in the memory 58, that is an indication of successful electrostimulation. Accordingly, a signal characterising stimulation success occurs at the output of the comparator 56 which is at the same time the output of the means 28 for stimulation outcome monitoring.

Analysing the derivative of the voltage at the means for stimulation outcome monitoring also provides de facto for determining the time constant for discharge of the coupling capacitor 24 and/or the Helmholtz capacitance 32 which is calculated as τ=R·C, that is to say from the product of the respective capacitance with ohmic tissue resistance plus possible further resistances such as the resistance 34.

In a preferred embodiment therefore the means 28 for stimulation outcome monitoring is adapted to determine the time constant of the R-C circuit which is operative when the short-circuit switch S3 is closed, and to evaluate it by threshold value comparison.

In individual cases, if it is assumed that all capacitances and resistances determining the discharge are combined together in a time constant T, the following is afforded for the autoshort voltage:

$$V_{auto}(t) = V_0 e^{\frac{1}{T}}.$$

That is to say, $$\frac{dV_{auto}}{dt} \frac{1}{V_{auto}} = -\frac{1}{T}$$

is thus inversely proportional to the time constant. After that conversion of the signal, it is possible to determine a variation in the time constant, for example, with an adaptive threshold value process. When such a process is adopted for example, a sliding mean value of the derived and standardised curve is formed. If a value of that curve exceeds the sliding mean value by a predetermined threshold value a change in the time constant is recognised.

A stimulus is thus recognised as effective if a variation in the discharge constant in a given time window is detected. The stimulus is assessed as being ineffective if that variation fails to appear. In that case a safety pulse is delivered and for example the pulse amplitude increased in accordance with a capture control algorithm.

In a particularly preferred embodiment provided on the part of the control unit 26 is a timer 60 which is started with the delivery of an electrostimulation pulse and which is stopped again with the occurrence of a signal characterising a stimulation success, on the part of the means 28 for stimulation outcome monitoring. The time detected in that manner by the timer 60 is a measurement of the degree to which an electrostimulation pulse is super-threshold, that is to say by how much the electrostimulation pulse is above the stimulus threshold of the myocardium. In the case of an only slightly super-threshold stimulation pulse the time detected by the timer 60 between the delivery of an electrostimulation pulse and the occurrence of stimulation success is longer than in the case of a greatly super-threshold stimulation pulse.

The control unit 26 is therefore preferably so designed that it causes a reduction in the stimulation pulse intensity, to save energy, if the time detected by the timer 60 is particularly short, for example shorter than a millisecond.

Figure 3A:
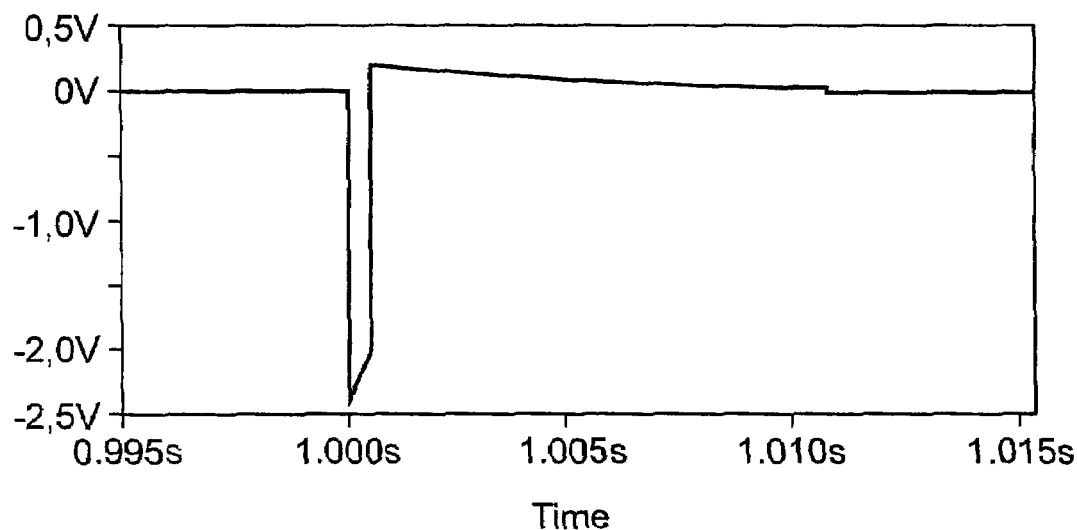
FIG. 3a shows an example of a signal which occurs upon successful stimulation at the input of the means for stimulation outcome monitoring.
Figure 3B:
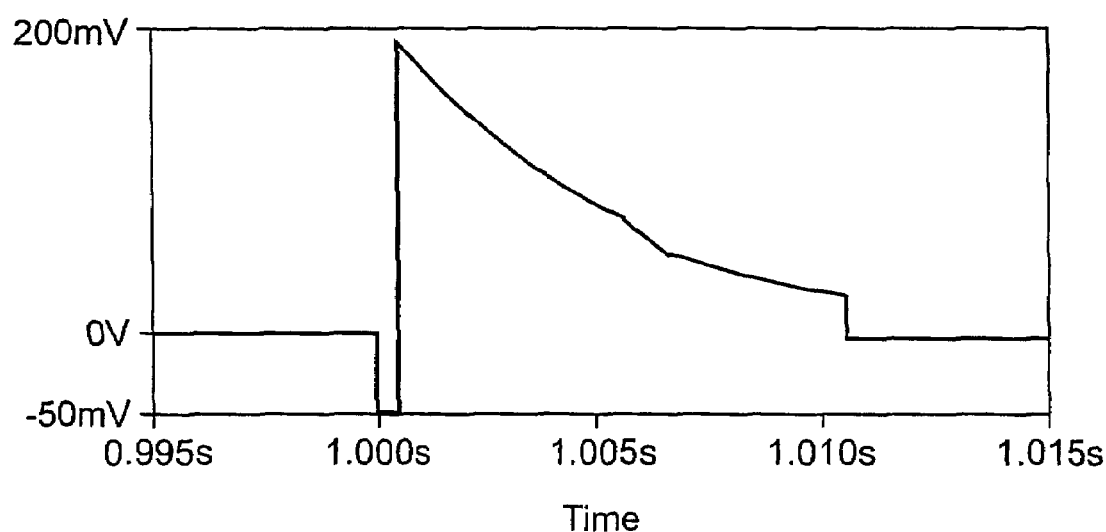
FIG. 3b shows a view on an enlarged scale of a portion of the signal from FIG. 3a, and FIG. 4 shows examples of signals which are derived from the signal of FIG. 3 within the means for stimulation outcome monitoring.

FIGS. 3a and b show by way of example the voltage detected by the means 28 for stimulation outcome monitoring in the event of successful electrostimulation. FIG. 3b in that respect is a view on an enlarged scale of a portion of FIG. 3a.

FIG. 4 shows the signal which occurs at the output of the differentiating member 52 (curve a) and at the output of the dividing member 54 (curve b) respectively.

What is claimed is:

1. A device for delivering electrical stimulation pulses to body tissue through a stimulation electrode, comprising:
   energy storage means for providing electrical stimulation energy to the stimulation electrode from an energy source;
   a first switch with which the energy storage means is switchably connected to the energy source for charging the energy storage means;
   an electrode connection for connecting the stimulation electrode to the device for delivering electrical stimulation pulses to the body tissue;
   a second switch with which the energy storage means is switchably connected to the electrode connection for the delivery of a stimulation pulse;
   means for monitoring stimulation outcome during a time interval between 0 milliseconds and 10 milliseconds after said delivery of a stimulation pulse, wherein said means for monitoring stimulation outcome does not use active measurement pulses from an active current source or an active voltage source;

a short-circuit switch with which the electrode connection, after delivery of the stimulation pulse, is switchably and at least indirectly connected to a ground potential such that, in the case of a connected and implanted electrode, a capacitance can be discharged by way of the body tissue wherein the capacitance includes at least one Helmholtz capacitance produced on the surface of the stimulation electrode in conjunction with surrounding body fluid or the body tissue; and a control unit which is connected to at least the first switch, the second switch, and the short-circuit switch for switching the respective switches and which is adapted to separate the electrode connection from the energy storage means after delivery of the stimulation pulse and at least indirectly connect the electrode connection to the ground potential;

wherein the means for monitoring stimulation outcome during said time interval is connected to the electrode connection and is adapted to detect a drop in a voltage during said time interval at the capacitance or a rise in a short-circuit current during said time interval at the capacitance, said drop in voltage or said rise in short-circuit current being representative of a characteristic drop in a myocardium impedance of said body tissue indicating stimulation success.

2. The device of claim 1, wherein:
the capacitance further comprises a coupling capacitor that is connected between the electrode connection and the ground potential when the short-circuit switch is closed.

3. The device of claim 2, wherein:
the coupling capacitor is arranged between the energy storage means and the electrode connection in such a way that the coupling capacitor is connected in series with the energy storage means when the second switch is closed.

4. The device of claim 3, wherein:
the means for monitoring stimulation outcome is arranged and adapted to detect the voltage at the coupling capacitor.

5. The device of claim 4, wherein:
the means for monitoring stimulation outcome is connected so as to detect at least one of a current strength of the short-circuit current over time or a level of the voltage over time at the capacitance between the coupling capacitor and the electrode connection.

6. The device of claim 5, wherein:
the means for monitoring stimulation outcome further comprises a differentiating member for differentiating the detected voltage level or the detected current strength.

7. The device of claim 6, wherein:
a threshold value detector is connected to the differentiating member in such a way that the means for monitoring stimulation outcome detects a drop in the detected voltage, which is above a predetermined limit value.

8. The device of claim 7, wherein:
a threshold value detector is connected to the differentiating member in such a way that the means for monitoring stimulation outcome ascertains when the derivative of the detected voltage is below a threshold value.

9. The device of claim 8, wherein:
a threshold value detector is connected to the differentiating member in such a way that the means for monitoring stimulation outcome detects when the derivative of the detected voltage, standardised to the detected voltage, is below a threshold value.

10. The device of claim 9, wherein:
a timer is connected to the means for monitoring stimulation outcome, the timer being started with the delivery of a stimulation pulse and which ascertains the time to the detection of a stimulation outcome.

11. The device of claim 10, wherein:
the timer outputs a time signal corresponding to the time duration between stimulation pulse output and occurrence of the stimulation outcome and is connected to the control unit which is responsive to the time signal and causes setting of a strength of the stimulation pulse in dependence on the time signal.

12. The device of claim 11, wherein:
the ground potential is formed by a housing of the device or a surface portion thereof.

13. The device of claim 12, wherein:
the energy storage means comprises at least one reservoir capacitor.

14. The device of claim 13, wherein:
the energy source includes a charge pump for charging the reservoir capacitor.

15. The device of claim 14, wherein:
said first switch switchably connects the energy source to the reservoir capacitor for charging the reservoir capacitor from the charge pump.

16. The device of claim 7, wherein:
a threshold value detector is connected to the differentiating member in such a way that the means for monitoring stimulation outcome detects when a derivative of the detected voltage, standardised to the detected voltage, is below a threshold value.

17. The device of claim 2, wherein:
the means for monitoring stimulation outcome further comprises a differentiating member for differentiating the detected voltage or the detected current.

18. The device of claim 17, wherein:
a threshold value detector is connected to the differentiating member in such a way that the means for monitoring stimulation outcome detects a drop in the detected voltage, which is above a predetermined limit value.

19. The device of claim 18, wherein:
a threshold value detector is connected to the differentiating member in such a way that the means for monitoring stimulation outcome ascertains when the derivative of the detected voltage is below a threshold value.

20. The device of claim 19, wherein:
a threshold value detector is connected to the differentiating member in such a way that the means for monitoring stimulation outcome detects when the derivative of the detected voltage, standardised to the detected voltage, is below a threshold value.

21. The device of claim 20, wherein:
a timer is connected to the means for monitoring stimulation outcome, the timer being started with the delivery of a stimulation pulse and which ascertains the time to the detection of a stimulation outcome.

22. The device of claim 21, wherein:
the timer outputs a time signal corresponding to the time duration between stimulation pulse output and occurrence of the stimulation outcome and is connected to the control unit which is responsive to the time signal and causes setting of a strength of the stimulation pulse in dependence on the time signal.

23. The device of claim 22, wherein:
the ground potential is formed by a housing of the device or a surface portion thereof.

24. The device of claim 23, wherein:

the energy storage means comprises at least one reservoir capacitor.

25. The device of claim 24, wherein:

the energy source includes a charge pump for charging the reservoir capacitor.

26. The device of claim 25, wherein:

said first switch switchably connects the energy source to the reservoir capacitor for charging the reservoir capacitor from the charge pump.

27. The device of claim 18, wherein:

a threshold value detector is connected to the differentiating member in such a way that the means for monitoring stimulation outcome detects when the derivative of the detected voltage, standardised to the detected voltage, is below a threshold value.

28. The device of claim 1, wherein:

a timer is connected to the means for monitoring stimulation outcome, the timer being started with the delivery of a stimulation pulse and which ascertains the time to the detection of a stimulation outcome.

29. The device of claim 28, wherein:

the timer outputs a time signal corresponding to the time duration between stimulation pulse output and occurrence of the stimulation outcome and is connected to the control unit which is responsive to the time signal and causes setting of a strength of the stimulation pulse in dependence on the time signal.

30. The device of claim 29, wherein:

the ground potential is formed by a housing of the device or a surface portion thereof.

31. The device of claim 30, wherein:

the energy storage means comprises at least one reservoir capacitor.

32. The device of claim 31, wherein:

the energy source includes a charge pump for charging the reservoir capacitor.

33. The device of claim 32, wherein:

said first switch switchably connects the energy source to the reservoir capacitor for charging the reservoir capacitor from the charge pump.

34. The device of claim 1, wherein:

the ground potential is formed by a housing of the device or a surface portion thereof.

35. The device of claim 34, wherein:

the energy storage means comprises at least one reservoir capacitor.

36. The device of claim 35, wherein:

the energy source includes a charge pump for charging the reservoir capacitor.

37. The device of claim 36, wherein:

said first switch switchably connects the energy source to the reservoir capacitor for charging the reservoir capacitor from the charge pump.

38. The device of claim 1, wherein:

the energy storage means comprises at least one reservoir capacitor.

39. The device of claim 38, wherein:

the energy source includes a charge pump for charging the reservoir capacitor.

40. The device of claim 39, wherein:

said first switch switchably connects the energy source to the reservoir capacitor for charging the reservoir capacitor from the charge pump.

\* \* \* \* \*